(12) United States Patent
Grass et al.

(10) Patent No.: US 7,595,421 B2
(45) Date of Patent: Sep. 29, 2009

(54) TRIPENTYL CITRATES AND THEIR USE

(75) Inventors: Michael Grass, Haltern am See (DE); Michael Woelk-Faehrmann, Marl (DE)

(73) Assignee: OXENO Olefinchemie GmbH, Marl (DE)

( * ) Notice: Subject to any disclaimer, the term of this patent is extended or adjusted under 35 U.S.C. 154(b) by 190 days.

(21) Appl. No.: 11/739,345

(22) Filed: Apr. 24, 2007

(65) Prior Publication Data

US 2007/0287781 A1 Dec. 13, 2007

(30) Foreign Application Priority Data

Jun. 8, 2006 (DE) .............. 10 2006 026 624

(51) Int. Cl.
*C07C 69/66* (2006.01)
*C08K 5/00* (2006.01)
(52) U.S. Cl. ................. 560/180; 524/284
(58) Field of Classification Search ......... 524/284; 560/180
See application file for complete search history.

(56) References Cited

U.S. PATENT DOCUMENTS

| 4,710,532 A * | 12/1987 | Hull et al. .......... 524/310 |
| 2002/0198402 A1* | 12/2002 | Bohnen et al. .......... 560/179 |
| 2004/0260113 A1 | 12/2004 | Bueschken et al. |
| 2005/0019214 A1* | 1/2005 | Schroeder et al. .......... 422/58 |
| 2005/0038285 A1 | 2/2005 | Maschmeyer et al. |
| 2005/0049341 A1* | 3/2005 | Grass et al. .......... 524/306 |
| 2005/0101800 A1 | 5/2005 | Buschken et al. |
| 2005/0198894 A1 | 9/2005 | Migdal et al. |
| 2006/0167151 A1 | 7/2006 | Grass et al. |
| 2007/0060768 A1 | 3/2007 | Grass et al. |
| 2007/0135665 A1* | 6/2007 | Wiese et al. .......... 585/16 |
| 2007/0266869 A1* | 11/2007 | Leonard et al. .......... 101/170 |

FOREIGN PATENT DOCUMENTS

| DE | 35 20 750 A1 | 2/1986 |
| DE | 198 42 370 A1 | 3/2000 |
| EP | 1 063 257 A1 | 12/2000 |
| WO | WO 03/008369 A1 | 1/2003 |
| WO | WO 2005/028407 A1 | 3/2005 |
| WO | WO2005080302 | * 9/2005 |
| WO | WO2005097925 | * 10/2005 |

OTHER PUBLICATIONS

U.S. Appl. No. 11/739,345, filed Apr. 24, 2007, Grass, et al.
U.S. Appl. No. 11/911,691, filed Oct. 16, 2007, Grass, et al.
U.S. Appl. No. 11/622,567, filed Jan. 12, 2007, Grass.
N. I. Salit, et al., "Esters of Citric and Malic Acids", Journal of General Chemistry of the USSR, vol. 33, No. 8, 1963, XP-008080925, pp. 2674-2676.
Database CA [Online], Chemical Abstracts, AN 1965:403591, XP-002443488, 1964, pp. 1-2.
Frank Alber, et al., "Citric acid esters based on mixtures of alcohol—New kind polymer additives and plasticizers for a variety of polymers", IP. COM Prior Art Database, [Online], XP-002443474, Jul. 13, 2004, pp. 1-11.

* cited by examiner

*Primary Examiner*—Mark Eashoo
*Assistant Examiner*—Angela C Scott
(74) *Attorney, Agent, or Firm*—Oblon, Spivak, McClelland, Maier & Neustadt, L.L.P.

(57) ABSTRACT

A tripentyl citrate having an optionally acylated, preferably acetylated, OH group, a process for making the tripentyl citrate, and the use of the tripentyl citrate as a plasticizer for plastics.

23 Claims, 1 Drawing Sheet

TRIPENTYL CITRATES AND THEIR USE

BACKGROUND OF THE INVENTION

1. Field of the Invention

The present invention relates to tripentyl citrates having an optionally acylated, preferably acetylated, OH group, a process for the preparation of the tripentyl citrates and the use of the tripentyl citrates as plasticizers.

2. Description of the Related Art

Polyvinyl chloride (PVC) is among the most economically important polymers. It is widely used both in the form of rigid PVC and in the form of flexible PVC.

To produce a flexible PVC, plasticizers are added to the PVC. In the majority of instances phthalic esters are used, particularly di-2-ethylhexyl phthalate (DEHP), diisononyl phthalate (DINP) and diisodecyl phthalate (DIDP).

Discussions about reproductive toxicity effects have in some instances already led to an increased level of identification marking under hazardous materials legislation and have also led to limitations on the use of certain phthalate plasticizers in toys for toddlers, and it therefore has to be assumed that the use of these phthalates will reduce markedly in the future, particularly in sensitive applications, such as food-or-drink packaging and medical applications. There is therefore a need for plasticizers which are not subject to identification-marking requirements and which can be used for example as DEHP replacement, and which are prepared from raw materials of which large quantities are available worldwide.

One conceivable alternative is the use of plasticizers based on citric acid. In particular, the best-known member of this class of compound, acetyl tri-n-butyl citrate (ATBC), has been increasingly used for the production of children's toys from flexible PVC, not least since certain phthalates have been subject to the abovementioned restriction on use. Another supporting factor here is the view taken by the Scientific Committee for Toxicology, Ecology and Ecotoxicology (CSTEE), which was an EU committee of toxicology experts, according to which the use of this plasticizer in flexible PVC toys is risk-free even for toddlers.

However, it is known that ATBC has higher volatility and migration rate than, for example, DEHP and therefore still has potential for optimization. There has therefore been no lack of attempts to develop structurally varied citric esters in which these disadvantages have been eliminated. In principle, this can be achieved via use of longer-chain alcohols for the esterification reaction. Examples of compounds which have long been known and also marketed are therefore acetyl tri-2-ethylhexyl citrate (ATEHC) or butyryl tri-n-hexyl citrate (BTHC). The preparation of ATBC is described by way of example in WO 03/008369, the entire contents of which are incorporated by way of reference into this application.

Alongside these, citrate esters having a free, i.e. non-acylated, OH group have also been described. By way of example, EP 1 063 257 mentions trialkyl esters of citric acid where alkyl=$C_6$ to $C_{10}$, the alkyl chains preferably being linear. When compared with their carboxylated analogues, these generally feature improved efficiency and gelling, but also feature poorer thermal stability.

Alongside the esters of citric acid or of acetylated citric acid with only one alcohol, such as butanol (i.e. ATBC) or 2-ethylhexanol (i.e. ATEHC), there also exist esters based on alcohol mixtures having different numbers of carbon atoms. Schär et al. describe, in Ip.com Journal (2004), 4 (8), pp. 15 et seq., the use of citric esters (having a free or derivatized OH group) based on alcohol mixtures which are composed of at least two different alcohols in the range from $C_2$ to $C_{22}$ and in which the alcohols are specifically mixed prior to the esterification reaction.

EP 1 256 566 describes mixtures of citric esters whose alkyl chains are composed of a certain percentage of butyl and a complementary percentage of longer radicals.

However, citric esters based on linear alcohols ($C_6$ and higher) are generally relatively expensive, since the alcohols have to be prepared via ethylene oligomerization or by way of fatty acid hydrogenation or hydrogenation of the fatty acid esters, e.g. methyl ester, whereas the use of competitively priced alcohols is a precondition for large-scale industrial production on the multiple-thousand-tonne scale. Longer-chain esters for example with $C_8$ alcohols have very low volatility but exhibit gelling which is too slow for certain plastisol-processing techniques. The relatively low efficiency is attended by a need to add relatively large amounts, and this generally contributes to a further increase in the cost of the formulation and to an increase in the amount of raw material consumed.

SUMMARY OF THE INVENTION

It is therefore one object of the invention to provide novel alternative plasticizers, preferably alternative citric esters, which preferably exhibit good processing properties, have good plasticizing action (efficiency), have only low volatility, and/or whose alcohols can readily and advantageously be prepared in large quantities.

It is another object of the invention to provide a process for making citric ester plasticizers.

It is another object of the invention to provide a composition comprising a citric ester plasticizer.

It is a further object of the invention to provide a PVC composition comprising the citric ester plasticizer.

DETAILED DESCRIPTION OF THE INVENTION

Figure 1:
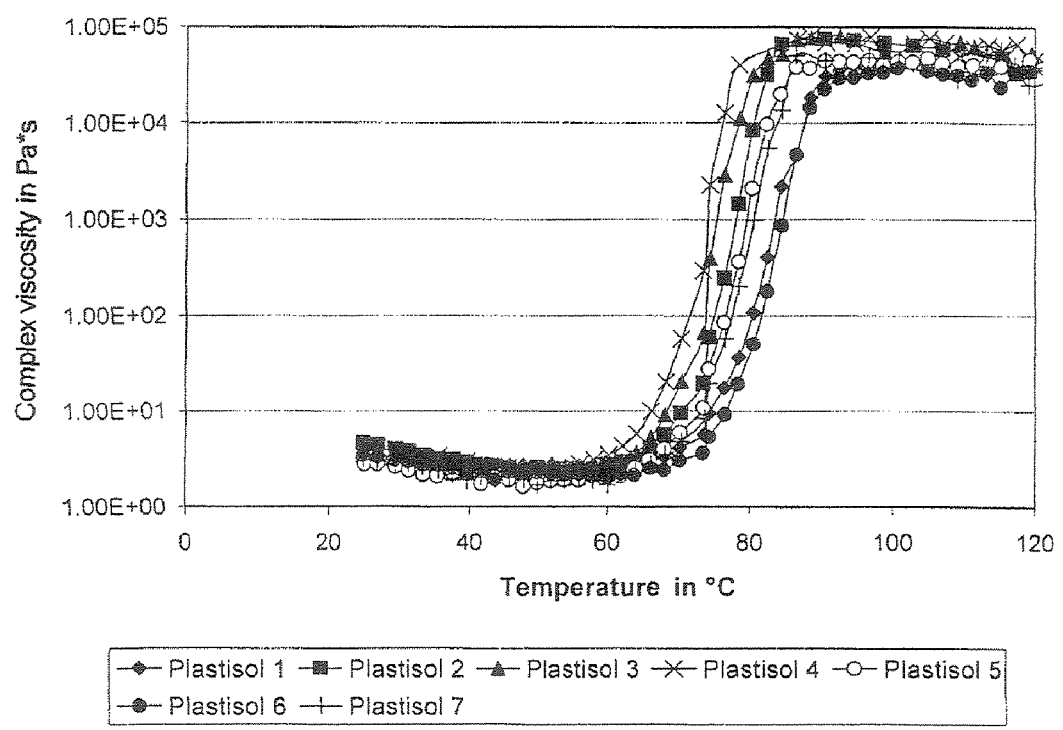
FIG. 1 shows the gelling curves of 7 plastisols.

Surprisingly, it has been found that pentyl esters of citric acid, in particular those having an acetylated OH group, meet one or more of the requirements mentioned above.

The present invention therefore provides citric esters of formula I

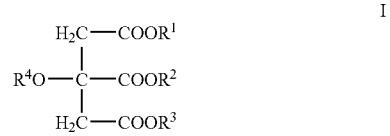

which are characterized in that each of the radicals $R^1$, $R^2$ and $R^3$ is an alkyl radical whose number of carbon atoms is 5 and the radical $R^4$ is H or a carboxylic acid radical, and provides a process for preparation of citric esters of the formula I, which is characterized in that citric acid or a citric acid derivative is reacted with an alcohol which has 5 carbon atoms.

The present invention also provides the use of the inventive citric esters as plasticizers.

The present invention also provides a composition comprising an inventive citric ester and the use of this composition or plasticizer composition in plastics compositions, in adhesives, in sealing compositions, in coatings, in paints, in plastisols or in inks. Examples of plastics products produced from the inventive plasticizers include: profiles, gaskets, food-or-drink packaging, foils, toys, medical items, roof sheeting, synthetic leather, floorcoverings, underbody protection, coated textiles, wallpapers, cables and wire sheathing.

An advantage of the inventive citric esters is that they can be used as "primary plasticizers". A "primary plasticizer" is usually, and for the purposes of the present invention, a plasticizer which is compatible with the appropriate polymer over a wide range of concentrations. When compared with ATBC, the inventive citric esters have markedly lower volatility at comparable efficiency, expressed by way of Shore hardness A.

When used as plasticizers the inventive citric esters can replace certain phthalates, e.g. di-2-ethylhexyl phthalate (DEHP). The volatility and gelling power of the inventive citrates is at a level similar to that of DEHP, which continues to be the most important PVC plasticizer worldwide. There are advantages in plastisol processing due to lower plastisol viscosity, even after prolonged storage. When comparison is made with DINP, the plasticizing action (efficiency) of the pentyl citrates and acetyl pentyl citrates is typically higher or, in the limiting case of pure acetyl tris(3-methylbutyl) citrate, at least identical.

Since the toxicological properties to be expected for tripentyl citrates or acetyl pentyl citrates are good and similar to those of ATBC, they may be used as a replacement for phthalates in particular in critical applications, such as children's toys or food-or-drink packaging. The inventive tripentyl citrates or acetyl pentyl citrates moreover have the advantage that they are based on an alcohol which is easy to prepare and whose raw material $C_4$ fraction or raffinate, is available in large quantities.

The invention is described below by way of example, but there is no intention that the invention, the scope of protection of which is apparent from the claims and from the description, be restricted thereto. The claims themselves are part of the disclosure content of the present invention. Where ranges, general formulae or classes of compounds are stated below, the intention is that the disclosure encompass not only the corresponding ranges or groups of compounds explicitly mentioned but also all of the subranges and subgroups of compounds which could be obtained by omitting individual values (ranges) or compounds, although these have not been explicitly mentioned for reasons of clarity.

A feature of the inventive citric esters of the formula I

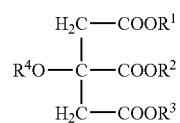

I is that each of the radicals $R^1$, $R^2$ and $R^3$ is an alkyl radical whose number of carbon atoms is 5 and the radical $R^4$ is H or a carboxylic acid radical. The radical $R^4$ is preferably a carboxylic acid radical, e.g. a formic acid radical, an acetic acid radical, a propionic acid radical, a butyric acid radical or a valeric acid radical. The radical $R^4$ is particularly preferably an acetyl radical. Carboxylated pentyl citrates have the advantage, when compared with the pentyl citrates having a free OH group, of being markedly more thermally stable, and this is by way of example apparent in delayed appearance of brown coloration (thus requiring less stabilization) in PVC foils plasticized therewith. Another advantage of the carboxylated pentyl citrates is that the viscosity rise in plastisols with time is, particularly if the acetylated esters are used, markedly smaller than with non-carboxylated pentyl citrates, and plastisols based on inventive carboxylated pentyl citrates therefore have better storage stability.

The alkyl radicals in an ester molecule can be identical or different. If the alcohols used in preparation of the esters are not isomerically pure, the product is usually mixtures of trialkyl esters of citric acid which comprise ester molecules which have different alkyl radicals.

It can be advantageous that the alkyl radicals $R^1$, $R^2$ and $R^3$ have a longest carbon chain of at least 4 carbon atoms and that their total number of carbon atoms per alkyl radical is 5. The term longest carbon chain is intended to represent the number of carbon atoms that are consecutively bonded to one another. In this embodiment of the invention branching of the longest carbon chain may occur so long as the number of consecutively bonded carbon atoms is preferably no more than 4. It is preferable that more than 60% of the alkyl radicals $R^1$, $R^2$ and $R^3$ are n-pentyl radicals wherein % is mole % based on the total number of moles of $R^1$, $R^2$ and $R^3$. The proportion of the pentyl radicals here is based on the average value of all of the alkyl radicals present in the citric esters. It is preferable that from 70 to 99.9% of the alkyl radicals of the citric esters are n-pentyl radicals and that from 30 to 0.1% are methylbutyl radicals, in particular 2-methylbutyl radicals, and it is particularly preferable that from 85 to 98% of the alkyl radicals of the citric esters are n-pentyl radicals and that from 15 to 2% are methylbutyl radicals, in particular 2-methylbutyl radicals, and it is very particularly preferable that from 90 to 96% of the alkyl radicals of the citric esters are n-pentyl radicals and that from 10 to 4% are methylbutyl radicals, in particular 2-methylbutyl radicals. It is preferable that more than 50%, with preference more than 75% and particularly preferably more than 95%, of the methylbutyl radicals are 2-methylbutyl radicals. However, as a function of raw material availability and intended use of the corresponding plasticizer, it can also be advantageous that at least 40%, preferably from 40 to 100%, particularly preferably from 50 to 99%, of the $C_5$-alkyl radicals of the citric esters are 3-methylbutyl radicals (all data in mol %).

The percentage distribution of the $C_5$-alkyl radicals can easily be determined via saponification of the esters, isolation of the resultant alcohol, and gas-chromatographic (GC) analysis of the resultant alcohol. By way of example, gas-chromatographic separation can be carried out on a polydimethylsiloxane column (e.g. DB 5) as stationary phase with length of 60 m, internal diameter of 0.25 mm and film thickness of 0.25 μm. As an alternative, this information can also be obtained by way of NMR spectroscopy.

The inventive citric esters can, for example, be prepared by the inventive process. A feature of this process for preparation of citric esters of the formula I

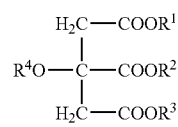

I in which process each of the radicals $R^1$, $R^2$ and $R^3$ is an alkyl radical whose number of carbon atoms is 5 and the radical $R^4$ is H or a carboxylic acid radical, is that citric acid or a citric acid derivative is reacted with an alcohol which has 5 carbon atoms. The reaction of the citric acid with the pentanols preferably takes place at a temperature above 120° C., preferably at from 120 to 160° C.

The citric esters can be prepared from the corresponding alcohols or alcohol mixtures via reaction with citric acid or with its derivatives. In particular, the citric esters can preferably be prepared via esterification using citric acid, e.g., using citric acid monohydrate or citric acid anhydrate, these being the forms in which citric acid is frequently commercially available, or else via transesterification starting from citric esters having relatively short alcohol radicals. Various processes for preparation of trialkyl citrates and of carboxy trialkyl citrates are known, and some of these were mentioned earlier above including WO 03/008369; EP 1063257; EP 1256566; and Ip.com Journal (2004), 468), pp. 15+. These can also be used for preparation of the inventive tripentyl citrates. Those publications are therefore expressly incorporated herein by way of reference. In the case of the transesterification reaction, an example of a starting material that can be used is trimethyl citrate or triethyl citrate.

Alcohols for preparation of the inventive citric esters can be any of the saturated alcohols which are composed of 5 carbon atoms and which have an OH group. It is preferable to use non-cyclic alcohols which have a longest carbon chain of at least 4 carbon atoms and whose total number of carbon atoms per alkyl radical is 5. Particular preference is given here to primary alcohols. By way of example, mention may be made here of n-pentanol, 2 methylbutanol and 3-methylbutanol and mixtures of these alcohols.

The inventive process preferably uses alcohol mixtures which comprise more than 60% by weight of n-pentanol based on the total weight of the alcohol mixture. It is preferable to use mixtures composed of n-pentanol and 2 methylbutanol in a ratio by weight of from 99.9 to 70% of n-pentanol to from 0.1 to 30% of methylbutanol, in particular 2-methylbutanol, particularly preferably of from 98 to 85% of n-pentanol to from 2 to 15% of methylbutanol, in particular 2-methylbutanol. However, as stated at an earlier stage above, as a function of raw material availability and intended use of the corresponding plasticizer it can also be advantageous to use alcohol mixtures which comprise at least 40% by weight, with preference from 40 to 100% by weight, particularly preferably from 50 to 99% by weight, of 3 methylbutanol.

The inventive process for preparation of citric esters of the formula I can preferably use primary alcohols or alcohol mixtures such as those obtainable via hydroformylation of an alkene with subsequent hydrogenation. By way of example, n-pentanol can be prepared via hydroformylation of 1-butene and subsequent hydrogenation of the valeraldehyde to give n-pentanol.

Precursors for pentanols are preferably industrial hydrocarbon mixtures which comprise one or more olefins having 4 carbon atoms. The most important source for $C_4$ olefins is the $C_4$ cut from steamcrackers. From this, after extraction (extractive distillation) of the butadiene or selective hydrogenation thereof to give a butene mixture, preferably an n-butene mixture, a hydrocarbon mixture (raffinate I or hydrogenated $C_4$ fraction) is prepared, comprising isobutene, 1-butene and the two 2 butenes (cis and trans). Another raw material for $C_4$ olefins is the $C_4$ cut from FCC plants, which can be worked up as described above. $C_4$ olefins prepared via Fischer-Tropsch synthesis are another suitable starting material, after selective hydrogenation of the butadiene present therein to give n-butenes. Olefin mixtures obtained via dehydrogenation of $C_4$ hydrocarbons or via metathesis reactions can also be suitable starting materials, as can other industrial olefin streams. Other precursors for the pentanols alongside raffinate I are raffinate II, raffinate III, a stream obtained via isolation of most of the 1-butene from raffinate II, and "crude butane", which is produced after oligomerization of raffinate II and in which the only olefin present alongside alkanes is small amounts of 2-butene. The advantage of using raffinate II, raffinate III or crude butane as precursor for pentanols is that these precursors comprise no, or almost no, isobutene, and the resultant pentanols therefore comprise no, or only small, amounts (less than 0.5% by weight, based on the pentanols) of 3-methylbutanol. If the intention is that the $C_5$ alcohols comprise greater proportions of 3-methylbutanol, it is possible to use pure isobutene as can be obtained by way of example via cleavage of methyl tert-butyl ether or of tert-butanol, or to use raffinate I or $C_4$ fraction directly.

Since the cost of separating the starting mixtures is often very high, it can be advantageous not to separate the olefins present in the industrial mixture to be used as starting mixture, but instead to use the mixtures directly.

The inventive process particularly preferably uses alcohol which is obtained via a process comprising the steps of
a) hydroformylation of $C_4$ olefins to give $C_5$ aldehydes and
b) hydrogenation of the aldehydes obtained in step a) to give the corresponding alcohols.

Steps a) and b) here can also be carried out simultaneously in a reactor.

It can be advantageous that, after step a) (hydroformylation) and/or b) (hydrogenation), the product mixtures obtained in these stages of the process are separated to give the individual isomers. This separation can take place thermally, for example, in particular via distillation.

Step a) of the Process

The hydroformylation of all of the olefins in the starting mixture can take place in one stage. This can be advantageous particularly when only one olefinic compound is present in the starting mixture for the hydroformylation reaction. By way of example, starting mixtures in which the only olefin present is 1-butene or isobutene can be hydroformylated in one stage under the conditions described below for the first stage, using the catalyst described there. By way of example, starting mixtures in which the only olefin present is 2-butene can be hydroformylated in one stage under the conditions described below for the second stage, using the catalyst described there.

However, since the starting mixtures are frequently not isomerically pure olefins but are mostly the industrial mixtures described above of $C_4$ hydrocarbons, step a) of the inventive process preferably uses a mixture of olefins which comprises isobutene and/or 1-butene and 2-butenes.

The hydroformylation of the olefins present in the starting mixture can in turn take place in one stage. For this, it is preferable to use a catalyst which can hydroformylate olefins having a different position of the double bond and/or a different number of branches. However, catalysts suitable for this purpose mostly give only low selectivity for formation of products (aldehydes, alcohols, formates) resulting from terminal hydroformylation and/or exhibit excessively low reaction rate for an industrial process.

If the intention is to obtain starting alcohols, in particular pentanols or pentanol mixtures, with minimum degree of branching from the hydroformylation products, it is advantageous to carry out the hydroformylation reaction in such a way as to obtain a high proportion of products produced via terminal hydroformylation, because it is only the terminally hydroformylated products which have the same degree of branching as their starting olefins, whereas the degree of branching of the product produced increases by 1 in the case of non-terminal hydroformylation, and in many instances this can lead to impairment of the performance characteristics of the downstream products prepared therefrom.

The olefins present in an industrial mixture differ considerably in their reactivity during hydroformylation. Olefins having terminal double bonds are generally more reactive than olefins having internal double bonds and linear olefins are generally more reactive than branched olefins. A rule which applies specifically in the case of the $C_4$ olefins is that 1 butene is more reactive than isobutene and isobutene is more reactive than the two 2-butenes (cis and trans). This differing reactivity can be utilized to obtain a high proportion of products produced via terminal hydroformylation, i.e. the intention is to produce mainly valeraldehyde rather than 2-methylbutanal from 1-butene, to produce 3-methylbutanal rather than 2,2-dimethylpropanal from isobutene and to maximize production of valeraldehyde (n-pentanal) from the two 2-butenes while producing little 2-methylbutanal.

Since there is still no catalyst available which brings about, simultaneously and at a satisfactory rate, not only the reaction of 1-butene but also that of isobutene and of the 2-butenes to give products produced via terminal hydroformylation, the hydroformylation reaction is preferably carried out in at least two stages, in particular if the two starting mixtures comprise not only isobutene and/or 1-butene but also 2-butenes. If the inventive process is carried out in two stages, it is preferable that isobutene and/or 1-butene is hydroformylated in one stage and that 2-butenes are hydroformylated in the other stage.

In a first stage, the hydroformylation reaction is preferably undertaken using a suitable catalyst under conditions where only α-olefins (1-butene, isobutene), but not the 2-butenes, are reacted to give the corresponding aldehydes. These conditions are preferably selected in such a way that 1-butene is converted with maximum selectivity to valeraldehyde and isobutene is converted with maximum selectivity to 3-methylbutanal. Examples of catalysts that can be used are compounds which contain rhodium and contain triorganic phosphorus compounds, in particular phosphines, as ligands. The reaction can be carried out in a homogeneous phase (analogously to the UCC process described in EP 0 562 451) or in a heterogeneous phase (analogously to the Rhone-Poulenc-Ruhrchemie process described in DE 26 27 354 and EP 0 562 451 each of which is incorporated herein by reference in its entirety). The first stage of step a) of the process is preferably carried out by the second method because catalyst separation is easier. The reaction temperatures for the first stage of step a) of the process are preferably from 70 to 150° C., with preference from 100 to 130° C. The process pressures are preferably from 2 to 20 MPa, with preference from 3 to 6 MPa.

The hydroformylation of the 1-olefins can optionally be carried out using high superficial velocities in a multiphase system where starting material, product and synthesis gas have been dispersed in a continuous catalyst phase. Processes of this type are described by way of example in DE 199 25 384 A1 and DE 199 57 528 A1, each of which are expressly incorporated herein by way of reference in their entirety.

The hydroformylation of the 1-olefins in the first stage of step a) of the process can be carried out in one or two stages. In the case of two-stage hydroformylation, 1-butene is mainly reacted in the first reactor and isobutene is mainly reacted in the second reactor. The two reactors can use the same catalysts or different catalysts. If the same catalysts are used, catalysts can be worked up together.

After the hydroformylation described immediately above of 1-butene and of portions of the isobutene in the first stage of step a) of the process, materials remaining in the starting hydrocarbon mixture comprise, if present, the 2-butenes and, if appropriate, isobutene and at most traces of 1-butene. This mixture can be hydroformylated as it stands, using another catalyst system, or after separation into two fractions, of which one comprises isobutene and the other comprises the two 2-butenes. The mixture is preferably separated, and the fraction comprising isobutene and the fraction comprising the 2-butenes are preferably hydroformylated separately.

The isobutene or the fraction comprising isobutene can be hydroformylated with high selectivities to give 3-methylbutanal. Suitable catalysts for this purpose are rhodium complexes which contain mono- or polydentate phosphite ligands. Examples of suitable monodentate phosphite ligands are triaryl phosphites whose aryl groups have both a bulky group in ortho-position with respect to the phosphite oxygen and also a substituent in m- or p-position, an example being tris(2,4-di-tert-butylphenyl)phosphite. By way of example, the patent specifications U.S. Pat. No. 4,668,651, U.S. Pat. No. 4,769,498 and WO 85/03702, each of which are expressly incorporated herein by way of reference in their entireties, describe hydroformylation of isobutene using a catalyst system composed of rhodium and of a bisphosphite.

Optionally, the isobutene fraction removed can be entirely or to some extent returned to the upstream first hydroformylation stage. It can be particularly advantageous here to remove the saturated hydrocarbons from the isobutene, and this can take place thermally, for example. After this removal of the saturated hydrocarbons, it can be particularly advantageous to return all of the isobutene to the upstream first hydroformylation stage.

The hydroformylation of 2-butenes and, respectively, of fractions comprising 2-butenes can be carried out with the aid of various known catalysts, the usual product being a mixture composed of 2-methylbutanal and valeraldehyde. In most cases, 2-methylbutanal is the main product. The use of unmodified cobalt catalysts as catalyst for the hydroformylation of 2 butenes is described in EP 0 646 563, and the use of unmodified rhodium is described in EP 0 562 451 each of which is incorporated herein by reference in its entirety. Furthermore, a catalyst system the same as that used for the hydroformylation of isobutene can be used for the hydroformylation of 2-butenes, namely a complex composed of rhodium and monodentate triaryl phosphite. High selectivities in terms of valeraldehyde can be obtained by using a catalyst composed of rhodium and of bulky aromatic bisphosphites, this being by way of example as described in EP 0 213 639, EP 0 214 622 or U.S. Pat. No. 5,763,680 each of which is incorporated herein by reference in its entirety. However, the reaction rates are relatively low for an industrial process. A bisphosphite ligand whose use is particularly preferred is the ligand termed ligand D in U.S. Pat. No. 5,763,680.

As stated above, the olefins present in the starting material can be hydroformylated separately or together. If the linearity of the final products is not of great importance, it is advantageous to hydroformylate the olefins together. In contrast, if minimum branching is desired in the final product, it is preferable to carry out the hydroformylation in at least two stages. In the case of a $C_4$ olefin mixture, the latter case implies that 1-butene and if appropriate isobutene is reacted in the first reactor and the remaining olefins are optionally reacted in the downstream reactor(s).

Known processes can be used to remove the catalyst from the hydroformylation mixtures. By way of example, the catalyst can be removed by distillation in the case of processes where the rhodium catalyst is present homogeneously in the reaction mixture. Phase separation can, for example, be used to remove the catalyst in the case of the reaction in a heterogeneous phase (two liquid phases) (see Ed. B. Comils, W. A. Herrmann, Applied Homogeneous Catalysis with Organic Compounds, Vol. 1, p. 80, VCH-Verlag, 1996 incorporated herein by reference in its entirety).

Step b) of the Process

After catalyst removal, the hydroformylation mixtures can either be directly used in the hydrogenation reaction or else can be separated in advance by distillation or by other separation methods into two or more fractions. In particular, it can be advantageous to work up the hydroformylation mixture in such a way as to give one or more fractions in essence comprising aldehydes.

The hydroformylation mixtures after catalyst removal or the aldehydes or fractions comprising aldehyde removed from these mixtures via a separation process, e.g., distillation, are hydrogenated according to the invention. The hydroformylation mixtures can be hydrogenated separately or together here. Hydrogenation produces the corresponding saturated alcohols from the aldehydes. Examples of these are butanols, n-pentanol, 2-methylbutanol and 3 methylbutanol.

The hydrogenation reaction can use nickel catalysts, copper catalysts, copper/nickel catalysts, copper/chromium catalysts, copper/chromium/nickel catalysts, zinc/chromium catalysts, or nickel/molybdenum catalysts, for example. The catalysts can be unsupported, or the substances active in hydrogenation and, respectively, their precursors can have been applied to supports, e.g. silicon dioxide or aluminium dioxide. Preferred catalysts used in step b) of the process and on which the hydroformylation mixtures can be hydrogenated comprise in each case from 0.3 to 15% by weight of copper and nickel and also as activators from 0.05 to 3.5% by weight of chromium and optionally from 0.01 to 1.6% by weight, preferably from 0.02 to 1.2% by weight, of an alkali metal component on a support material, preferably aluminium oxide and silicon dioxide based on the total weight of the catalyst. The quantities stated are based on the catalyst prior to reduction. The alkali metal component is optional. The catalysts are advantageously used in a form in which they have low flow resistance, e.g. in the form of granules, pellets or mouldings, such as tablets, cylinders, strand extrudates or rings. Prior to use, they are advantageously activated, e.g. via heating in a stream of hydrogen.

The hydrogenation reaction can be a gas-phase or liquid-phase hydrogenation reaction. The hydrogenation reaction is preferably carried out at a total pressure of from 0.5 to 50 MPa, preferably from 1.5 to 10 MPa. A gas-phase hydrogenation reaction can also be carried out at lower pressures, the gas volumes present then being correspondingly large. If a plurality of hydrogenation reactors is used, the total pressures in the individual reactors can be identical or different within the pressure limits mentioned. The reaction temperatures during the liquid- or gas-phase hydrogenation reaction can generally be from 120 to 220° C., in particular from 140 to 180° C. Hydrogenation reactions of this type are described by way of example in patent applications DE 198 42 369 and DE 198 42 370, each of which are expressly incorporated herein by reference in their entireties.

The hydrogenation reaction is preferably carried out in the presence of water. The water needed can be present in the reactor feed. However, it is also possible to feed water at a suitable point into the hydrogenation apparatus. In the case of gas-phase hydrogenation, water is advantageously introduced in the form of steam. A preferred hydrogenation process is liquid-phase hydrogenation with addition of water, this hydrogenation being described by way of example in DE 100 62 448 incorporated herein by reference in its entirety. The hydrogenation reaction is particularly preferably carried out with water content of from 0.05 to 10% by weight, in particular from 0.5 to 5% by weight, very particularly preferably from 1 to 2.5% by weight based on the total weight of the reaction mixture. The water content here is determined in the material discharged from the hydrogenation reaction.

The mixtures obtained from the hydrogenation reaction can either be directly used for the reaction with citric acid or citric acid derivative or else can be separated by distillation or by other separation methods to give two or more fractions. In particular, it can be advantageous to work up the hydrogenation mixture in such a way as to give one or more fractions of alcohols with the same number of carbon atoms. The distillative work-up can preferably be carried out in such a way as to give substantial separation into the individual constituents.

If the intention is to prepare a citric ester from linear alcohols as starting alcohols, linear n pentanol can be separated out from the branched pentanols.

Step c) of the Process: Reaction of Citric Acid or Citric Acid Derivative with $C_5$ Alcohol to Give Tripentyl Citrate Reaction of the $C_5$ alcohols to give the corresponding tripentyl citrate can take place via reaction with citric acid, which by way of example can be used in the form of the monohydrate or in anhydrous form (anhydrate), or via reaction with a derivative of citric acid, in particular with a citric ester. It is preferable to esterify citric acid or to transesterify citric esters using the alcohol obtained from step b).

By way of example, the inventive citric esters can be obtained via esterification of citric acid, which can by way of example be used in the form of the monohydrate or in anhydrous form (anhydrate), using the corresponding alcohols. The alcohol and, respectively, the alcohol mixture used to form the ester can simultaneously serve as entrainer for removal of the water produced during the reaction and is preferably used in excess, a preferred excess used being from 5 to 50%, in particular from 10 to 40%, particularly preferably from 15 to 35%, of the molar amount needed for formation of the ester.

The esterification reaction is preferably carried out in the presence of an esterification catalyst. Esterification catalysts that can be used are in principle acids, such as sulphuric acid, sulphonic acids, e.g., methanesulphonic acid or p-toluenesulphonic acid, mineral acids, or metals or their compounds. Examples of those suitable are tin, titanium, zirconium, which can be used in the form of finely divided metals or advantageously in the form of their salts or oxides or in the form of soluble organic compounds. However, in comparison with the catalysts based on proton acids, the metal catalysts are high-temperature catalysts which often do not achieve their full activity until temperatures above 180° C. have been reached. It is preferable to use sulphuric acid or organic sulphonic acids, and it is particularly preferable to use methanesulphonic acid.

The catalyst concentration can be varied widely as a function of the nature of the catalyst. Concentrations of from 0.05 to 2% by weight are advantageous for proton acids, preferably from 0.1 to 1% by weight, particularly preferably from 0.15 to 0.5% by weight based on the total weight of the reaction mixture. Although higher concentrations increase the reaction rate, they can also, however, contribute to an increased level of by-product formation, for example via elimination of water.

As previously mentioned in the abovementioned publications, citric acid and, respectively, its alkyl esters have a tendency toward elimination of water at relatively high temperature (>153° C.) to form aconitic acid and its esters (aconitates). The processes described above have therefore been operated generally at temperatures below 150° C. There are therefore also only a few cases where metal-based acids, such as tetrabutyl orthotitanate, are used for this purpose.

At temperatures below 150° C. it is possible by way of example to carry out operations using the proton acids described above, but the reaction time for the esterification reaction of citric acid monohydrate with, for example, n-butanol is then frequently above 10 hours (WO 03/008369 incorporated herein by reference in its entirety).

Surprisingly, it has now been found that the esterification of citric acid, preferably anhydrous citric acid and particularly preferably citric acid monohydrate, with the pentanols or pentanol mixtures prepared in step b) of the process had proceeded almost quantitatively after as little as 8 hours at from 155 to 165° C., with catalysis by proton acids, among which particular preference is given to methanesulphonic acid, and that the resultant product had, after conventional work-up, purity levels comparable with the prior art, in particular with those stated in WO 03/008369.

The ideal temperatures for carrying out the esterification of the starting materials are generally dependent on the progress of the reaction and on the catalyst concentration and type of catalyst. The ideal temperatures for each individual case can readily be determined via simple preliminary experiments. Use of higher temperatures can increase the reaction rate, but side reactions are favoured, an example being elimination of water from alcohols or formation of coloured by-products.

In the case of the inventive pentyl citrates, the reaction temperature is preferably from 120 to 180° C., with preference from 130 to 170° C. and particularly preferably from 155 to 165° C.

The desired reaction temperature or the desired temperature range can be set via appropriate adjustment of the pressure in the reaction vessel. The esterification reaction is preferably carried out for the purposes of the present invention at a pressure of from 0.1 MPa to 1 hPa.

In order to remove the water of reaction, it can be advantageous to remove the water from the reaction mixture by distillation in the form of a mixture, e.g. in the form of an azeotropic mixture with the alcohol. The amount of liquid to be returned to the reaction can be composed to some extent or entirely of alcohol obtained via work-up of the distillate. It is also possible to carry out the work-up at a later juncture and to replace the amount of liquid removed entirely or to some extent by fresh alcohol, i.e., alcohol provided in a feed vessel. It is preferable that the amount of liquid removed from the reaction mixture is replaced by alcohol.

The crude ester mixtures, which comprise not only the ester(s) but also alcohol, catalyst or its downstream products and, if appropriate, by-products, can be worked up by methods known per se. The work-up here preferably comprises one or more of the following steps: removal of excess alcohol and, if appropriate, low boilers, washing of the crude product with water or with an aqueous salt solution, neutralization of the unreacted acids, optionally a steam distillation, conversion of the catalyst to a readily filterable residue, removal of the solids and, if appropriate, drying. The sequence of these steps can differ as a function of the work-up method used.

Optionally, the desired ester can be separated by distillation from the reaction mixture, if appropriate after neutralization of the batch. This can be advantageous particularly in the case of products which are solid at room temperature.

In another embodiment of the inventive process, the inventive tripentyl citrates can be obtained via transesterification of a citric ester with a starting alcohol selected from isomerically pure pentanols or a suitable pentanol isomer mixture. The starting materials used comprise citric esters whose alkyl radical bonded to the O atom of the ester group preferably has from 1 to 3 carbon atoms. This radical can be aliphatic, straight-chain or branched, alicyclic or aromatic. One or more methylene groups of this alkyl radical can be substituted by oxygen. It can be advantageous for the boiling point of the alcohols on which the starting ester is based to be lower than that of the starting alcohols. A preferred starting material is triethyl citrate, which is produced industrially and is therefore available in large quantities.

The transesterification reaction is preferably carried out at a temperature of from 100 to 220° C. The temperature selected is particularly preferably sufficiently high that the alcohol produced from the starting ester can be removed from the reaction mixture by distillation at the prescribed pressure, preferably an increased pressure.

The work-up of the transesterification mixtures can take place in exactly the manner described for the esterification mixtures.

Step d) of the Process: Optional Carboxylation of the OH Group of the Citric Acid or of the Citric Ester If the intention in the inventive process is to prepare esters having a radical $R^4$ which is not H, the reaction of the OH group of the citric acid with another carboxylic acid or with an anhydride can take place prior to or after the reaction, preferably after the reaction, of the citric acid or of the citric acid derivative with the alcohol. The reaction carried out can be a simple esterification reaction. The esterification reaction preferably takes place with use of alkanoic acids, such as acetic acid, propionic acid or butyric acid, or particularly preferably using acetic anhydride. By way of example, the process of acetylation of the citric ester can take place as described in DE-B 10 99 523 incorporated herein by reference in its entirety. The acetylation preferably comprises the steps of acetylation with an excess of acetic anhydride, removal of excess acetic anhydride, and also, if appropriate, of acetic acid formed, by distillation, neutralization with a base (e.g. soda solution, sodium hydroxide solution or potassium hydroxide solution, milk of lime, etc.), washing, drying, decolorizing (e.g. via treatment with bleaching earth, ozone or hydrogen peroxide) and filtration. As a function of the method and sequence used, some of the steps mentioned here are merely optional.

The carboxylation, preferably the acetylation, of the OH group of the citric acid or of the citric ester preferably takes place after the removal of the excess alcohol via distillation with subsequent steam treatment of the citric ester prepared. If necessary, further purification steps can be carried out prior to the acetylation reaction, but this is preferably not necessary.

In the case of the acetylation reaction, this is preferably carried out via addition of a molar excess of from 10 to 80%, preferably from 20 to 50%, of acetic acid or preferably acetic anhydride at temperatures of from 90 to 120° C., preferably from 100 to 115° C. At the same time as, or after, addition of the carboxylating agent, a proton acid is preferably added as catalyst, and the reaction mixture is stirred at this temperature for a certain time, preferably from 30 minutes to 2 hours, in particular 1 hour. A very wide variety of acids can be used here as catalyst. Sulphuric acid or methanesulphonic acid is preferably used as catalyst. The excess acid or the anhydride is then removed and products can be worked up conventionally (neutralization, if appropriate washing, steam distillation, drying, filtration).

The inventive citric esters can be used as plasticizers, in particular in plastics compositions, in adhesives, in sealing compositions, in coatings, in paints, in plastisols, in synthetic leathers, in floorcoverings, in underbody protection, in coated textiles, in wallpapers, or in inks, as plasticizer. The inventive plasticizers can preferably be used in profiles, in gaskets, in food-or-drink packaging, in foils, in toys, in medical items, in roof sheeting, in synthetic leathers, in floorcoverings, in underbody protection, in coated textiles, in wallpapers, in cables and in wire sheathing, and particularly preferably in food-or-drink packaging, in toys, in medical items, in wallpapers and in floorcoverings.

Use of the inventive citric esters can in particular give inventive compositions which comprise a citric ester.

The compositions of the invention may comprise the inventive citric ester alone or in a mixture with other plasticizers. If the inventive compositions comprise the inventive citric esters in a mixture with other plasticizers, the other plasticizers can preferably have been selected from the group of the dialkyl esters of phthalic acid, preferably having from 4 to 13 carbon atoms in the alkyl chain; trialkyl esters of trimellitic acid, preferably having from 6 to 10 carbon atoms in the side chain; dialkyl esters of adipic acid, and preferably dialkyl esters of terephthalic acid, in each case preferably having from 4 to 10 carbon atoms in the side chain; alkyl esters of 1,2-cyclohexanedioic acid, alkyl esters of 1,3-cyclohexanedioic acid and alkyl esters of 1,4-cyclohexanedioic acid, and preferably alkyl esters of 1,2-cyclohexanedioic acid, in each case preferably where alkyl=alkyl radical having from 7 to 10 carbon atoms in the side chain; dibenzoic esters of glycols; alkylsulphonic esters of phenol preferably having an alkyl radical which contains from 8 to 22 carbon atoms; polymeric plasticizers; glycerol esters and very particularly preferably trialkyl esters of citric acid having a free or carboxylated OH group and having an alkyl radical of 4 or from 6 to 10 carbon atoms, and alkyl esters of benzoic acid, preferably having from 7 to 13 carbon atoms in the alkyl chain. In all cases, the alkyl radicals can be linear or branched and identical or different. The composition particularly preferably comprises not only esters of citric acid but in particular an alkyl ester of benzoic acid where alkyl=alkyl radical having from 7 to 13 carbon atoms, preferably isononyl benzoate, nonyl benzoate, isodecyl benzoate or decyl benzoate. The proportion of inventive citric esters in the mixture with other plasticizers is preferably from 15 to 90%, particularly preferably from 20 to 80% and very particularly preferably from 30 to 70%, where the proportions by weight of all of the plasticizers present give a total of 100%.

Compositions containing the citric ester of the invention and of other plasticizers may be used as plasticizers in plastics compositions, in adhesives, in coatings, in paints, in sealing compositions, in plastisols, or in inks. Examples of plastics products produced from the inventive plasticizer compositions can be: profiles, gaskets, food-or-drink packaging, foils, toys, medical items, roof sheeting, synthetic leather, floorcoverings, underbody protection, coated textiles, wallpapers, cables and wire sheathing. Among this group, products which may be given preferred mention are food-or-drink packaging, toys, medical items, wallpapers and floorcoverings.

The inventive compositions may further comprise one or more polymers selected from polyvinyl chloride (PVC), polyvinylidene chloride (PVDC), polyacrylates, in particular polymethyl methacrylate (PMMA), polyalkyl methacrylate (PAMA), fluoropolymers, in particular polyvinylidene fluoride (PVDF), polytetrafluorooethylene (PTFE), polyvinyl acetate (PVAc), polyvinyl alcohol (PVA), polyvinyl acetals, in particular polyvinyl butyral (PVB), polystyrene polymers, in particular polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, in particular polyethylene (PE) or polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, in particular polylactic acid (PLA), polyhydroxybutyric acid (PHB), polyhydroxyvaleric acid (PHV), polyesters, starch, cellulose and cellulose derivatives, in particular nitrocellulose (NC), ethylcellulose (EC), cellulose acetate (CA), cellulose acetate/butyrate (CAB), rubber or silicones, and also mixtures or copolymers of the polymers mentioned or of their monomeric units. The inventive compositions preferably comprise PVC and/or homo- and/or copolymers based on ethylene, and/or propylene, and/or butadiene, and/or vinyl acetate, and/or glycidyl acrylate, and/or glycidyl methacrylate, and/or methacrylates, and/or acrylates, and/or acrylates or methacrylates having, bonded to the oxygen atom of the ester group, alkyl radicals of branched or unbranched alcohols having from 1 to 10 carbon atoms, and/or styrene, and/or acrylonitrile or and/or cyclic olefins.

The PVC grade preferably present in the inventive composition comprises suspension PVC, bulk PVC, microsuspension PVC or emulsion PVC. The inventive compositions preferably comprise, based on 100 parts by weight of polymer, from 5 to 200 parts by weight of plasticizer, preferably from 10 to 150 parts by weight.

The inventive compositions can comprise not only the constituents mentioned but also further constituents, in particular by way of example other plasticizers, fillers, pigments, stabilizers, co-stabilizers, such as epoxidized soya bean oil, lubricants, blowing agents, kickers, antioxidants or biocides.

The compositions comprising the polymers mentioned can be used as plastics compositions, adhesives, sealing compositions, coatings, paints, plastisols, synthetic leather, floorcoverings, underbody protection, textile coatings or wallpapers, or inks, or for their production. The compositions mentioned can in particular be profiles, gaskets, food-or-drink packaging, foils, toys, medical items, roof sheeting, synthetic leather, floorcoverings, underbody protection, coated textiles, wallpapers, cables and wire sheathing. The compositions are preferably food-or-drink packaging, toys, medical items, wallpapers and floorcoverings.

FIG. 1 provides further illustration of the invention, but there is no intention that the invention be restricted to the types of embodiment shown by way of example in that figure.

FIG. 1 shows gelling curves for the 7 plastisols tested in example 8. Complex viscosity is plotted as a function of temperature. The values measured for plastisol 1 are characterized by diamonds, the values measured for plastisol 2 are characterized by squares, the values measured for plastisol 3 are characterized by triangles, the values measured for plastisol 4 are characterized as X, the values measured for plastisol 5 are characterized as open circles, the values measured for plastisol 6 are characterized as filled circles and the values measured for plastisol 7 are characterized as crosses.

The examples below are intended to illustrate the invention without restricting the breadth of application apparent from the description and from the patent claims.

EXAMPLES

The syntheses described in Examples 1 and 2 for the citric esters were carried out starting from pentanols commercially available (FLUKA), namely n-pentanol (GC purity>99% by weight), 2-methylbutanol (>98% by weight) and 3-methylbutanol (>98.5% by weight). The alcohols or alcohol mixtures stated in Table 1 were used to prepare the various esters.

TABLE 1

Alcohols or alcohol mixtures used in Examples 1 and 2.

| n-Pentanol | 2-Methylbutanol | 3-Methylbutanol | Corresponding ester | Number |
|---|---|---|---|---|
| 100% | 0% | 0% | Tri-n-pentyl citrate | 1 A |
| 100% | 0% | 0% | Acetyl tri-n-pentyl citrate | 2 A |
| 0% | 0% | 100% | Acetyl tri(3-methylbutyl) citrate | 2 B |
| 90% | 10% | 0% | Acetyl tripentyl citrate | 2 C |

The % data are % by weight based on the total weight of all pentanols.

Since isomeric compounds are involved here and require no adaptation of the stoichiometrically required amounts, the general term pentanols is used hereinafter for simplicity.

Example 1

Preparation of Tripentyl Citrates 210 g (1 mol) of citric acid monohydrate (Riedel de Haen, purity >99.5% by weight) and initially 300 g of a total of 352 g of pentanol or pentanol mixture (4 mol) according to Table 1 were used as initial charge in a 2 litre multiple-neck flask with stirrer, water separator, dropping funnel, internal thermometer and immersion tube. Nitrogen gas was first introduced for 30 minutes for flushing by way of the immersion tube, and then the system was slowly heated. Starting at about 115° C., the water of crystallization from the acid was initially produced, and was removed by way of the water separator. When a temperature of 145° C. was reached, 0.63 g of methanesulphonic acid dissolved in the remaining 52 g of pentanol or pentanol mixture was added by way of the dropping funnel (under nitrogen). When the reaction temperature of 160° C. was reached, a constant return of the pentanol/water mixture was set via successive reduction of pressure. After about 8 hours, the acid number was <1 mg KOH/g (DIN EN ISO 2114) and the esterification reaction was concluded.

The water separator was then—still under nitrogen—replaced by a distillation bridge and the excess alcohol was removed by distillation at 160° C. under a slowly increasing vacuum.

For work-up, the mixture was cooled to 100° C. 200 ml of 5% strength by weight sodium chloride solution were then added to the reaction mixture, and the mixture was stirred at 80° C. for 15 minutes. The aqueous phase was then removed and the mixture was again washed with the same amount of sodium chloride solution and the phases were again separated. After the second washing procedure, the acid number was determined to DIN EN ISO 2114 and nine times the stoichiometric amount of 5% strength by weight sodium hydroxide solution were used for neutralization for 30 minutes at 80° C., with stirring. The aqueous phase was then discharged and 5% strength by weight sodium chloride solution was again used twice as described above for washing.

After phase separation, the crude ester mixture was again heated to 160° C. and 8% by weight of deionized water, based on the expected amount of crude ester, were slowly added dropwise by way of the immersion tube at this temperature in vacuo. Care was taken here that the temperature did not rise above 160° C. The system was then filled with nitrogen, 2% by weight of powdered activated charcoal were added, and the system was cooled under renewed vacuum (extending to 5 hPa) to 80° C. and the product was then filtered.

Purity: 99% by area (determined via gas chromatography)

Example 2

Preparation of Acetyl Tripentyl Citrates 210 g (1 mol) of citric acid monohydrate (Riedel de Haen) and initially 300 g of a total of 352 g of pentanol or pentanol mixture (4 mol) according to Table 1 were used as initial charge in a 2 litre multiple-neck flask with stirrer, water separator, dropping funnel, internal thermometer and immersion tube. Nitrogen gas was first introduced for 30 minutes for flushing by way of the immersion tube, and then the system was slowly heated. Starting at about 115° C., the water of crystallization from the acid was initially produced, and was removed by way of the water separator. When a temperature of 145° C. was reached, 0.63 g of methanesulphonic acid dissolved in the remaining 52 g of pentanol or pentanol mixture was added by way of the dropping funnel (under nitrogen). When the reaction temperature of 160° C. was reached, a constant return of the pentanol/water mixture was set via successive reduction of pressure. After about 8 hours, the acid number was <1 mg KOH/g (DIN EN ISO 2114) and the esterification reaction was concluded.

The water separator was then—still under nitrogen—replaced by a distillation bridge and the excess alcohol was removed by distillation at 160° C. under a slowly increasing vacuum.

The water separator was then replaced, under nitrogen, by a distillation bridge, and the apparatus was again evacuated. 8% by weight of deionized water, based on the expected amount of crude ester, were then added dropwise by way of the dropping funnel and the immersion tube. Once all of the water had been added, the system was cooled to 110° C. in vacuo (<5 mbar).

For acetylation, 1.25 times the molar amount of acetic anhydride were used. The theoretical amount of crude ester was utilized for the calculation.

For addition of the acetic anhydride, the apparatus was filled with nitrogen and flushed with nitrogen for 5 minutes. The acetic anhydride was slowly added by way of the dropping funnel. 0.5 g of methanesulphonic acid was then added slowly at from 100° C. to 110° C. and stirring was continued for a further hour. Acetic acid and excess acetic anhydride were then removed by distillation at 130° C. or below under a carefully adjusted vacuum.

For work-up, the mixture was cooled to 100° C. 200 ml of 5% strength by weight sodium chloride solution were then added to the reaction mixture, and the mixture was stirred at 80° C. for 15 minutes. The aqueous phase was then removed and the mixture was again washed with the same amount of sodium chloride solution and the phases were again separated. After the second washing procedure, the acid number was determined to DIN EN ISO 2114 and nine times the stoichiometric amount of 5% strength by weight sodium hydroxide solution were used for neutralization for 30 minutes at 80° C., with stirring. The aqueous phase was then discharged and 5% strength by weight sodium chloride solution was again used twice as described above for washing.

After phase separation, the crude ester mixture was again heated to 160° C. and 8% by weight of deionized water, based on the expected amount of crude ester, were slowly added dropwise by way of the immersion tube at this temperature in vacuo. Care was taken here that the temperature did not rise above 160° C. The system was then filled with nitrogen, 2% by weight of powdered activated charcoal were added, and the system was cooled under renewed vacuum (extending to 5 hPa) to 80° C., and the material was stirred at this temperature for about 30 minutes with 2% by weight of hydrogen peroxide and then dried at 120° C. and then again cooled and filtered.

Example 3

Preparation of Plastisols

The starting weights used of the components for the various plastisols are found in Table 2 below.

TABLE 2

| Mixing specifications according to Example 3 (all data in phr (= parts by weight per 100 parts by weight of PVC)) | | | | | | | |
|---|---|---|---|---|---|---|---|
| Plastisol mixing specification | 1 | 2 | 3 | 4 | 5 | 6 | 7 |
| Vestolit B 7021 (Vestolit GmbH) | 100 | 100 | 100 | 100 | 100 | 100 | 100 |
| Vestinol 9 (DINP from OXENO Olefinchemie) | 50 | | | | | | |
| DEHP (OXENO Olefinchemie GmbH) | | 50 | | | | | |
| Acetyl tri-n-butyl citrate (Jungbunzlauer) | | | 50 | | | | |
| Tri-n-pentyl citrate (according to the invention, 1 A) | | | | 50 | | | |
| Acetyl tri-n-pentyl citrate (according to the invention, 2 A) | | | | | 50 | | |
| Acetyl-tri(3-methylbutyl) citrate (according to the invention, 2 B) | | | | | | 50 | |
| Acetyl tripentyl citrate (according to the invention, 2 C) | | | | | | | 50 |
| Epoxidized soyabean oil (Drapex 39, Crompton) | 3 | 3 | 3 | 3 | 3 | 3 | 3 |
| Mark CZ 140 (Crompton) | 1.5 | 1.5 | 1.5 | 1.5 | 1.5 | 1.5 | 1.5 |

The temperature of the plasticizers was brought to 25° C. prior to addition. First, the liquid constituents were weighed into a PE beaker and then the pulverulent constituents were weighed in. The mixture was mixed manually with a paste spatula until all the powder had been wetted. The mixing beaker was then clamped into the clamping equipment of a dissolver mixer. Prior to immersing the stirrer into the mixture, the rotation rate was set at 1800 revolutions per minute. Once the stirrer had been switched on, stirring was continued until the temperature on the digital display of the temperature sensor reached 30.0° C. This ensured that the plastisol was homogenized with defined energy input. The temperature of the plastisol was then immediately brought to 25° C.

Example 4

Viscosity Measurements and Storage Stabilities

The viscosities of the plastisols prepared in Example 3 were measured as follows by a method based on DIN 53 019 using a Physica DSR 4000 rheometer (Paar-Physica), which is controlled by way of the associated US 200 software.

The plastisol was again stirred with a spatula in the storage container and tested in the Z3 test system (DIN 25 mm) according to the operating instructions. The test proceeded automatically by way of the abovementioned software at 25° C. The following conditions were applied:

pre-shear of 100 $s^{-1}$ for a period of 60 s without recording any test values a downward gradient starting at 200 $s^{-1}$ extending downward as far as 0.1 $s^{-1}$, divided into a logarithmic series with 30 steps with in each case a measurement point duration of 5 s.

The test data were automatically processed by the software after the test. Viscosity was shown as a function of shear rate. The tests were carried out after each of 2 h, 4 h, 24 h and 28 days. The paste was stored at 25° C. between these junctures.

Table 3 below lists by way of example for the shear rate of 100 $s^{-1}$ in each case the corresponding viscosity values obtained after the stated storage times.

TABLE 3

| Shear rate 100 $s^{-1}$ (Viscosities stated in Pa * s) | | | | | | |
|---|---|---|---|---|---|---|
| Plastisol mixing specification | Plasticizer used | 2 h | 4 h | 24 h | 28 d | Total rise from 2 h after 28 days in % |
| 1 | DINP (Vestinol 9) | 3.59 | 3.68 | 6.51 | 8.22 | 129 |
| 2 | DEHP | 4.04 | 4.13 | 7.44 | 11.2 | 177 |
| 3 | Acetyl tri-n-butyl citrate (Jungbunzlauer) | 2.84 | 2.87 | 5.67 | 8.58 | 202 |
| 4 | Tri-n-pentyl citrate (according to the invention, 1 A) | 2.49 | 2.69 | 5.24 | 11.3 | 354 |
| 5 | Acetyl tri-n-pentyl citrate (according to the |  2.63 | 2.70 | 4.80 | 6.63 | 152 |

TABLE 3-continued

Shear rate 100 s$^{-1}$ (Viscosities stated in Pa * s)

| Plastisol mixing specification | Plasticizer used | 2 h | 4 h | 24 h | 28 d | Total rise from 2 h after 28 days in % |
|---|---|---|---|---|---|---|
| | invention, 2 A) | | | | | |
| 6 | Acetyl tri-3-methylbutyl citrate (according to the invention, 2 B) | 4.47 | 4.47 | 7.96 | 9.72 | 117 |
| 7 | Acetyl tripentyl citrate (according to the invention, 2 C) | 2.81 | 2.83 | 4.93 | 6.81 | 142 |

Example 5

Preparation of Castings for Shore Hardness Tests

Shore A hardness is a measure of the softness of a test specimen. The greater the possible penetration of a standardized needle into the test specimen during a test of a certain duration, the lower the test value. The plasticizer with the highest efficiency gives the lowest Shore hardness value, for an identical amount of plasticizer. Conversely, in the case of very efficient plasticizers it is possible to save a certain proportion in the mixing specification, and in many cases this means lower costs for processors.

To determine Shore hardness values, the plastisols prepared according to Example 3 were poured into circular casting moulds whose diameter was 50 mm. The plastisols in the moulds were then gelled at 200° C. for 10 min a drying cabinet with air circulation, and were removed after cooling and stored under standard conditions of temperature and humidity (23° C.; 50% relative humidity) for at least 16 hours prior to testing. The thickness of the sheets was about 8 mm.

The tests themselves were carried out by analogy with DIN 53 505 using a Shore A tester from Zwick-Roell, the test value being in each case read off after 3 seconds. Three different measurements were carried out at different points on each test specimen (not in the edge region) and in each case the average was noted. The test values obtained are listed in Table 4.

TABLE 4

Results of Shore A hardness determination

| Plastisol mixing specification | Plasticizer used | Shore A hardness |
|---|---|---|
| 1 | Vestinol 9 | 83 |
| 2 | DEHP | 81 |
| 3 | Acetyl tri-n-butyl citrate (Jungbunzlauer) | 79 |
| 4 | Tri n-pentyl citrate (according to the invention, 1 A) | 76 |
| 5 | Acetyl tri-n-pentyl citrate (according to the invention, 2 A) | 79 |
| 6 | Acetyl tri(3-methylbutyl) citrate (according to the invention, 2 B) | 83 |
| 7 | Acetyl tripentyl citrate (according to the invention, 2 C) | 79 |

Example 6

Determination of Thermal Stability

In this test, the test specimens were exposed to elevated temperatures in the region of processing temperatures. The time prior to occurrence of marked discoloration serves as a measure of the thermal stability of the mixing specification. Colourless specimens discolour by way of yellow and brown in the direction of black via elimination of hydrogen chloride (HCl) and formation of polyene segments.

Production of Foils:

To produce the test specimens, foils of thickness 1 mm were first produced for each mixing specification. For this, high-gloss release paper (Sappi, Italy) was first cut to a size of 30*44 cm and was then placed in the clamping frame of the LTSV coating equipment for a Mathis oven. The clamping frame was then placed on the guide frame, the Mathis oven (LTF) was set to 200° C., and once this temperature had been reached the frame was preheated for 15 seconds. The doctor was then placed in the clamping apparatus and the doctor gap was adjusted by way of preliminary experiments in such a way that the thickness of the foil after conclusion of gelling was 1 mm (+/−0.05 mm). An adhesive strip was applied to the front edge of the paper in order to intercept excess paste. The paste was then applied in front of the doctor and was spread (speed about 6 m/min) by drawing the guide frame with the doctor over the clamped release paper. The doctor was then removed and the adhesive strip with the excess paste was taken away. The melt roll was then lowered and the clamping frame was run into the oven. After gelling (2 minutes at 200° C.), the frame was run back out of the oven and, after cooling, the foil was peeled from the paper.

Specimen Preparation:

The foils of thickness 1 mm were cut with scissors to 20*20 mm. Fifteen test specimens were needed per mixing specification. These were then placed in sequence on the test frame. The temperature of the Mathis thermotester was set to 200° C., and the test frame was run in and run back out of the oven at a constant velocity. In this way, each of the test specimens could be run out from the oven at an interval of 1.5 minutes, thus permitting variation of thermal exposure of the test specimens in a chronologically defined manner. All of the test specimens had been run back out of the oven after 23 minutes (including the control specimen).

The test specimens, as defined according to mixing specification and residence time in the oven, were mounted on card and fastened in a folder to permit comparison.

Table 5 below lists the results of thermal stability testing. In each case the juncture prior to intense black coloration is stated.

TABLE 5

Results of thermal stability determination

| Plastisol mixing specification | Plasticizer used | Juncture prior to black coloration in minutes (residence time in oven) |
|---|---|---|
| 1 | Vestinol 9 | 16.5 |
| 2 | DEHP | 16.5 |
| 3 | Acetyl tri-n-butyl citrate (Jungbunzlauer) | 16.5 |
| 4 | Tri-n-pentyl citrate (according to the invention, 1 A) | 12 |

TABLE 5-continued

Results of thermal stability determination

| Plastisol mixing specification | Plasticizer used | Juncture prior to black coloration in minutes (residence time in oven) |
|---|---|---|
| 5 | Acetyl tri-n-pentyl citrate (according to the invention, 2 A) | 16.5 |
| 6 | Acetyl tri-3-methylbutyl citrate (according to the invention, 2 B) | 16.5 |
| 7 | Acetyl tripentyl citrate (according to the invention, 2 C) | 15 |

As can readily be seen from the data in Table 5, the plastisol mixing specification in which a pentyl citrate having a free OH group was used as plasticizer has the poorest thermal stability.

Example 7

Measurement of Volatility from the Foil by a Method Based on DIN 53 407

The foils produced in Example 6 whose thickness was about 1 mm are in each case used to stamp out three discs with diameter 50 mm, these being first stored for 24 h in standard conditions of temperature and humidity (23° C./50% relative humidity) and then weighed. Using a method based on DIN 53 407, the discs are then in each case heated at 80° C. in a heating cabinet for 24 hours (Method A, direct contact with activated charcoal, grain size 2.5 mm). The discs are then in turn removed from the heating cabinet, cooled for 24 hours under standard conditions of temperature and humidity, and again weighed before they are again stored in the heating cabinet. The test ends after a heating period of 7*24 hours. Table 6 lists the test values obtained:

The volatility of the specimens which comprise the inventive plasticizers tri-n-pentyl citrate (1A) and acetyl tripentyl citrate (2A, 2C) is comparable with that of DEHP, therefore providing a marked advantage in comparison with ATBC.

Example 8

Determination of Gelling Behaviour

The gelling behaviour of the plastisols was studied in a Bohlin CVO oscillation viscometer (PP20 measurement system), operated using shear-stress control.

The following parameters were set:

Mode: Temperature gradient
　Start temperature: 25° C.
　End temperature: 180° C.
　Heating/cooling rate: 2° C./min
　Temperature after measurement: 25° C.
　Oscillation frequency: 2 Hz
　Delay time: 1 s
　Waiting time: 15 s
　Continuous oscillation: on
　Automatic input of shear stress: on
　Starting shear stress: 0.3 Pa
　Intended deformation: 0.002
　Gap width 0.5 mm Conduct of Test:

The spatula was used to apply a drop of the plastisol mixing specification to be tested, with no air bubbles, to the lower plate of the test system. Care was taken here that it was possible for some plastisol to expand out from the test system uniformly (not more than about 6 mm around the periphery) after the test system had been closed together. The protective covering, which also serves for thermal insulation, was then applied and the test was started.

The variable known as complex viscosity of the plastisol was plotted as a function of the temperature. Onset of the

TABLE 6

Results of volatility measurement

| Plastisol mixing specification | Plasticizer used | 1 d | 2 d | 3 d | 4 d | 5 d | 6 d | 7 d |
|---|---|---|---|---|---|---|---|---|
| 1 | Vestinol 9 | 0.65 | 0.9 | 1.26 | 1.69 | 2.09 | 2.24 | 2.48 |
| 2 | DEHP | 1.28 | 2.04 | 2.89 | 3.88 | 4.80 | 5.41 | 6.11 |
| 3 | Acetyl tri-n-butyl citrate (Jungbunzlauer) | 3.17 | 5.29 | 7.40 | 9.44 | 11.20 | 12.40 | 13.60 |
| 4 | Tri-n-pentyl citrate (according to the invention, 1 A) | 1.43 | 2.12 | 3.02 | 4.09 | 5.18 | 5.70 | 6.35 |
| 5 | Acetyl tri-n-pentyl citrate (according to the invention, 2 A) | 1.26 | 1.82 | 2.58 | 3.54 | 5.31 | 5.69 | 6.21 |
| 6 | Acetyl tri-3-methylbutyl citrate (according to the invention, 2 B) | 1.75 | 2.71 | 4.25 | 5.50 | 7.10 | 7.74 | 8.54 |
| 7 | Acetyl tripentyl citrate (according to the invention, 2 C) | 1.15 | 1.70 | 2.53 | 3.51 | 4.43 | 4.99 | 5.56 | gelling process was discernible in a sudden sharp rise in complex viscosity. The earlier the onset of this viscosity rise, the better the gellability of the system.

FIG. 1 presents the gelling curves for the seven plastisols. It can be seen that the inventive tripentyl citrate provides the best gelling performance. Although this is somewhat reduced via acetylation, it continues to be comparable with that of DEHP and better than that of DINP. Replacement of a proportion, 10 mol %, of n-pentanol by 2-methylbutanol has no significant effect. Rapidity of gelling is practically the same with acetyl tri(3-methylbutyl)citrate as with DINP.

German application DE 102006026624.2 filed on Jun. 8, 2006 is incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

The invention claimed is:

1. A mixture of citric esters of the formula I,

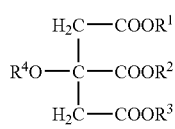

wherein each of the radicals $R^1$, $R^2$ and $R^3$ is an alkyl radical whose number of carbon atoms is 5 and the radical $R^4$ is H or a carboxylic acid radical,
wherein more than 60 mol % of $R^1$, $R^2$ and $R^3$ are n-pentyl radicals and from 30 to 0.1 mol % of $R^1$, $R^2$ and $R^3$ are methylbutyl radicals.

2. The mixture of citric esters according to claim 1, wherein from 70 to 99.9 mol % of $R^1$, $R^2$ and $R^3$ are n-pentyl radicals and from 30 to 0.1 mol % of $R^1$, $R^2$ and $R^3$ are methylbutyl radicals.

3. The mixture of citric esters according to claim 2, wherein from 85 to 98 mol % of $R^1$, $R^2$ and $R^3$ are n-pentyl radicals and from 15 to 2 mol % of $R^1$, $R^2$ and $R^3$ are methylbutyl radicals.

4. The mixture of citric esters according to claim 2, wherein methylbutyl radicals are 2-methylbutyl radicals.

5. The mixture of citric esters according to claim 1, wherein $R^4$ is a carboxylic acid radical.

6. The mixture of citric esters according to claim 5, wherein $R^4$ is an acetyl radical.

7. A process for making the mixture of citric esters of claim 1, comprising:
reacting citric acid or a citric acid derivative with an alcohol mixture having 5 carbon atoms.

8. The process according to claim 7, further comprising: forming the alcohol mixture by
a) hydroformylating one or more $C_4$ olefins to form one or more $C_5$ aldehydes, and then
b) hydrogenating the $C_5$ aldehydes to form the alcohols.

9. The process according to claim 8, wherein the hydroformylating a) is carried out on a mixture of olefins comprising one or more of an isobutene, a 1-butene and a 2-butene.

10. The process according to claim 8, wherein the hydroformulating a) is carried out in two stages,
(i) hydroformylating at least one of isobutene and 1-butene, and
(ii) hydroformylating one or more 2-butenes.

11. The process according to claim 7, wherein the hydrogenating is carried out in the presence of a catalyst comprising from 0.3 to 15% by weight of copper and from 0.3 to 15% by weight of nickel and, as an activator, from 0.05 to 3.5% by weight of chromium and optionally from 0.01 to 1.6% by weight of an alkali metal component, on a support material.

12. A plasticizer, comprising:
as a plasticizer, the mixture of citric esters according to claim 1.

13. A product selected from the group consisting of a plastic composition, an adhesive, a sealing composition, a coating, a paint, a plastisol, a synthetic leather, a floorcovering, an underbody protection, a coated textile, a wallpaper, an ink, a profile, a gasket, a food-or-drink package, a foil, a toy, a medical item, a roof sheeting, a cable and a wire sheathing, said product comprising the plasticizer according to claim 12.

14. A composition comprising as a plasticizer, the mixture of citric esters according to claim 1.

15. The composition according to claim 12, further comprising at least one additional plasticizer selected from the group consisting of a dialkyl ester of phthalic acid, a trialkyl ester of trimellitic acid, a dialkyl ester of adipic acid, a dialkyl ester of terephthalic acid, an alkyl ester of 1,2-cyclohexanedioic acid, an alkyl ester of 1,3-cyclohexanedioic acid, an alkyl ester of 1,4-cyclohexanedioic acid, a dibenzoic ester of glycols, an alkylsulphonic ester of a phenol, a polymeric plasticizer, a glycerol ester, a trialkyl ester of citric acid having a free or carboxylated OH group and having an alkyl radical of 4 or from 6 to 10 carbon atoms, and an alkyl ester of benzoic acid.

16. The composition according to claim 15, wherein the proportion of citric esters is from 15 to 90% by weight, where the proportion by weight of all of the plasticizers is 100%.

17. The composition according to claim 12, comprising at least one alkyl ester of benzoic acid wherein the alkyl group of the alkyl ester has from 7 to 13 carbon atoms.

18. The composition according to claim 17, wherein the alkyl ester of benzoic acid is at least one of isononyl benzoate, nonyl benzoate, isodecyl benzoate and decyl benzoate.

19. The composition according to claim 14, further comprising at least one material selected from the group consisting of a polyvinyl chloride, a polyvinylidene chloride, a polyacrylate, a fluoropolymer, a polyvinyl acetate, a polyvinyl alcohol, a polyvinyl acetal, a polystyrene polymer, a polyolefin, a thermoplastic polyolefin, a polyethylene-vinyl acetate, a polycarbonate, a polyethylene terephthalate, a polybutylene terephthalate, a polyoxymethylene, a polyamide, a polyethylene glycol, a polyurethane, a thermoplastic polyurethane, a polysulphide, a biopolymer, a polyester, a starch, a cellulose, a cellulose derivative, a rubber, a silicone, mixtures thereof and copolymers thereof.

20. The composition according to claim 19, comprising at least one material selected from the group consisting of a suspension PVC, a bulk PVC, a microsuspension PVC and an emulsion PVC.

21. The composition according to claim 14, further comprising at least one material selected from the group consisting of a different plasticizer, a filler, a pigment, a stabilizer, a lubricant, a blowing agent, a kicker, an antioxidant and a biocide.

22. The composition according to claim 14, wherein the composition is in the form of at least one of a plastic composition, an adhesive, a sealing composition, a coating, a paint, a plastisol, a synthetic leather, a floorcovering, an underbody protection, a coated textile, a wallpaper, an ink, a profile, a gasket, a food-or-drink packaging, a foil, a toy, a medical item, a roof sheeting, a cable, and a wire sheathing.

23. A mixture of citric esters of the formula I,

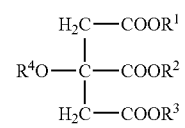

wherein each of the radicals $R^1$, $R^2$ and $R^3$ is an alkyl radical whose number of carbon atoms is 5 and the radical $R^4$ is H or a carboxylic acid radical,
wherein from 40% to 99% of the alkyl radicals $R^1$, $R^2$ and $R^3$ are 3-methylbutyl radicals.

* * * * *